United States Patent [19]

Craig et al.

[11] Patent Number: 4,910,406

[45] Date of Patent: Mar. 20, 1990

[54] METHOD FOR DETECTING THE PRESENCE OF CONTAMINANTS IN A REUSABLE PLASTIC FOOD OR BEVERAGE CONTAINER

[75] Inventors: Alan R. Craig; James E. Davis, both of Wilmington, Del.; John C. Steichen, Landenberg, Pa.

[73] Assignee: E. I. Du Pont De Nemours and Company, Wilmington, Del.

[21] Appl. No.: 291,585

[22] Filed: Dec. 29, 1988

Related U.S. Application Data

[63] Continuation-in-part of Ser. No. 171,972, Mar. 23, 1988, abandoned.

[51] Int. Cl.$^4$ ............................................. G01N 21/17
[52] U.S. Cl. .................................... 250/372; 250/301; 250/302; 250/461.1; 250/474.1; 422/55; 436/1
[58] Field of Search ............ 250/301, 302, 373, 461.1, 250/474.1; 422/55; 436/1, 2

[56] References Cited

U.S. PATENT DOCUMENTS

| | | | |
|---|---|---|---|
| 3,620,676 | 11/1971 | Davis | 422/57 |
| 3,732,079 | 5/1973 | Davis | 422/61 |
| 3,899,295 | 8/1975 | Halpern | 422/56 |
| 4,049,121 | 9/1977 | White | 206/439 |
| 4,166,044 | 8/1979 | Germonprez et al. | 252/408.1 |
| 4,179,397 | 12/1979 | Rohowetz et al. | 252/408.1 |
| 4,238,384 | 12/1980 | Blumberg et al. | 523/351 |
| 4,285,697 | 8/1981 | Neary | 250/339 |
| 4,298,569 | 11/1981 | Read | 422/27 |
| 4,368,980 | 1/1983 | Aldred et al. | 356/240 |
| 4,407,960 | 10/1983 | Tratnyek | 436/1 |
| 4,459,023 | 7/1984 | Reich et al. | 436/20 |
| 4,486,387 | 12/1984 | Augurt | 422/58 |
| 4,495,291 | 1/1985 | Lawton | 436/1 |
| 4,526,752 | 7/1985 | Perlman et al. | 422/56 |
| 4,551,627 | 11/1985 | Reich | 356/237 |
| 4,772,561 | 9/1988 | Genshaw | 436/169 |

FOREIGN PATENT DOCUMENTS

| | | | |
|---|---|---|---|
| 2141172 | 2/1973 | Fed. Rep. of Germany | 436/2 |
| 2823318 | 11/1979 | Fed. Rep. of Germany | 250/302 |

OTHER PUBLICATIONS

L. P. Shpaizman, L. G. Bogatkov, E. A. Shevchenko and B. M. Krasovitskii, "Luminescence Method of Determining Penetrations of Electrolytes into Polymeric Films," Translated from (Zhurnal Prikladnoi Spektroskopii), vol. 21, No. 1 (Jul. 1974), pp. 157-158 © 1976 Plenum Publishing Corporation, New York.

Primary Examiner—Constantine Hannaher

[57] ABSTRACT

This invention relates to a method for detecting whether contaminants are on or have migrated into the body of a plastic reusable food or beverage container. The invention uses a sensor attached to the inside of the container which changes optical density when it is exposed to certain contaminants. The change in optical density is detected by illuminating the sensor with ultraviolet light and then measuring the effect that the sensor has on the ultraviolet light.

23 Claims, 7 Drawing Sheets

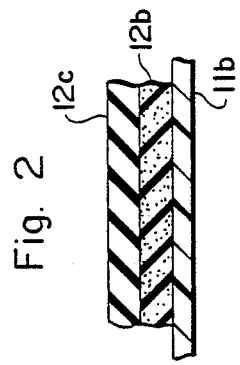
Fig. 2
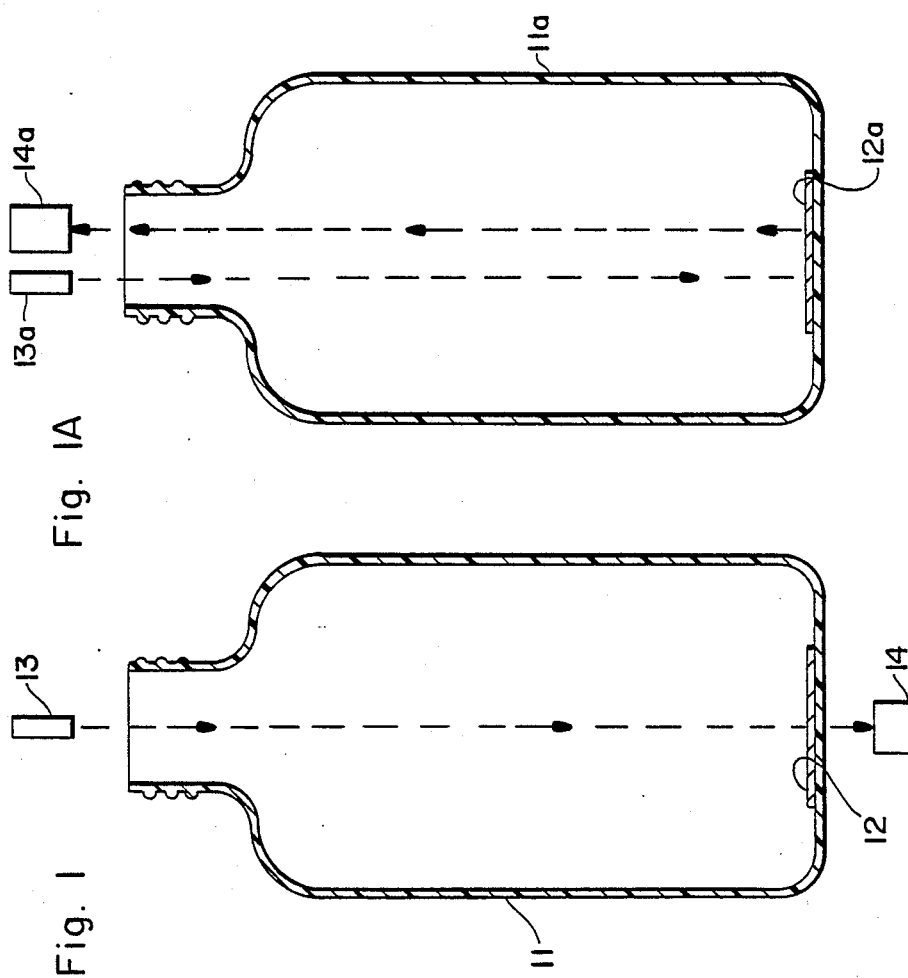
Fig. 1A
Fig. 1

METHOD FOR DETECTING THE PRESENCE OF CONTAMINANTS IN A REUSABLE PLASTIC FOOD OR BEVERAGE CONTAINER

CROSS-REFERENCE TO RELATED APPLICATIONS

This application is continuation-in-part of application Ser. No. 07/171,972 filed Mar. 23, 1988 now abandoned.

BACKGROUND OF THE INVENTION

This invention is related to an essentially instantaneous method for determining whether a polymeric food or beverage container has been exposed to certain contaminants. The discussion below will focus on beverage containers but the invention is also applicable to food containers.

Polymeric beverage containers that are potentially reusable and refillable are in use for a wide variety of soft drink beverages such as "Coke", "Diet Coke", "Pepsi", "Diet Pepsi", "7 Up", "Dr. Pepper", root beer, cream soda, "Sprite", "Regular Slice", "Diet Slice", gingerale and the like. It is expected that beer and other alcoholic beverages will be sold in reusable polymeric beverage containers in the future. Currently, billions of polymeric containers are used worldwide and their use is expected to grow.

These containers are formed from copolymers of acrylonitrile, polyethylene terephthalate (PET), amorphous nylon and multilayer composites, as well as more common moldable resins such as polyethylene and polypropylene. Unlike glass containers which do not absorb contaminants and are relatively easy to clean, the polymeric beverage container will absorb contaminants placed in the container. For example, pine oil or lemon oil will be absorbed by the polymeric container structure and when a beverage is placed in the container the contaminant will leach out into the beverage and impart the beverage with an off taste. A more serious problem arises when toxic substances are placed in the polymeric container such as lindane, parathion and the like. These substances are also absorbed by the polymeric container and can later leach into a beverage placed into the container. This problem has effectively precluded the widespread commercial reuse of polymeric containers.

Nevertheless, in order to conserve energy, materials and waste disposal space, the food and beverage industries in several countries are planning to begin to reuse these plastic containers. A major impediment to this effort lies in the difficulty of determining whether the polymeric container has been contaminated.

Prior art automatic inspection systems for beverage containers focus upon surface defects or residual liquid left in the container. For instance, there are inspection systems such as described in U.S. Pat. No. 4,459,023 issued to Reich et al on July 10, 1984, that determine if the container has dust, contamination or cracks on the container surface using a polarized scanned optical beam and an array of polaroid optical detectors. Other automatic inspection systems such as described in U.S. Pat. No. 4,368,980 issued to Alfred et al on Jan. 18, 1983 detect the presence of residual product or liquids, e.g., water and oil, remaining inside the container using the absorption of infrared radiation by water. Other prior art in this area focus upon color changes of a strip or cell exposed to a specific substance or atmosphere (e.g., ethylene oxide, steam, water, normal atmospheric conditions, etc.). In these references, the detection method is based upon visually sensing the change in color or configuration. None of the prior art inspection systems use a sensor attached to the inside of the container which is later illuminated with ultraviolet (UV) light to essentially instantaneously detect whether a number of different contaminants have potentially leached into the structure of a polymeric container.

In order to allow the large scale commercial reuse of polymeric food or beverage containers, there is a need for a method of detecting whether or not a polymeric container has been exposed to contaminants. Obviously, expensive analytical techniques and equipment can be used to analyze for contaminants but to be useful and practical the method must be inexpensive, essentially instantaneous and provide for easy and simple detection of a wide variety of contaminants.

SUMMARY OF THE INVENTION

A method for determining whether selected contaminants may have migrated into the body of a plastic reusable food or beverage container. This method involves attaching a sensor to the inside of the container. The sensor is designed to go through a detectable change in its optical density (opacity) when it is exposed to contaminants of interest. The sensor is then exposed to ultraviolet light and a light detector senses whether there has been a change in the optical density of the sensor.

BRIEF DESCRIPTION OF THE DRAWINGS

FIG. 1 shows a cross section of a polymeric container and sensor with the sensor attached to the inside of the bottom of the container. An ultraviolet light source is above the container, illuminating the sensor through the container opening and a light detector is on the other side of the sensor underneath of the container.

FIG. 1A is the same as FIG. 1 except that the light detector is placed beside the light source above the opening of the container.

FIG. 2 shows a partial cross section of the polymeric container and a two layered sensor attached to the container.

DETAILED DESCRIPTION OF THE INVENTION

Figure 3:
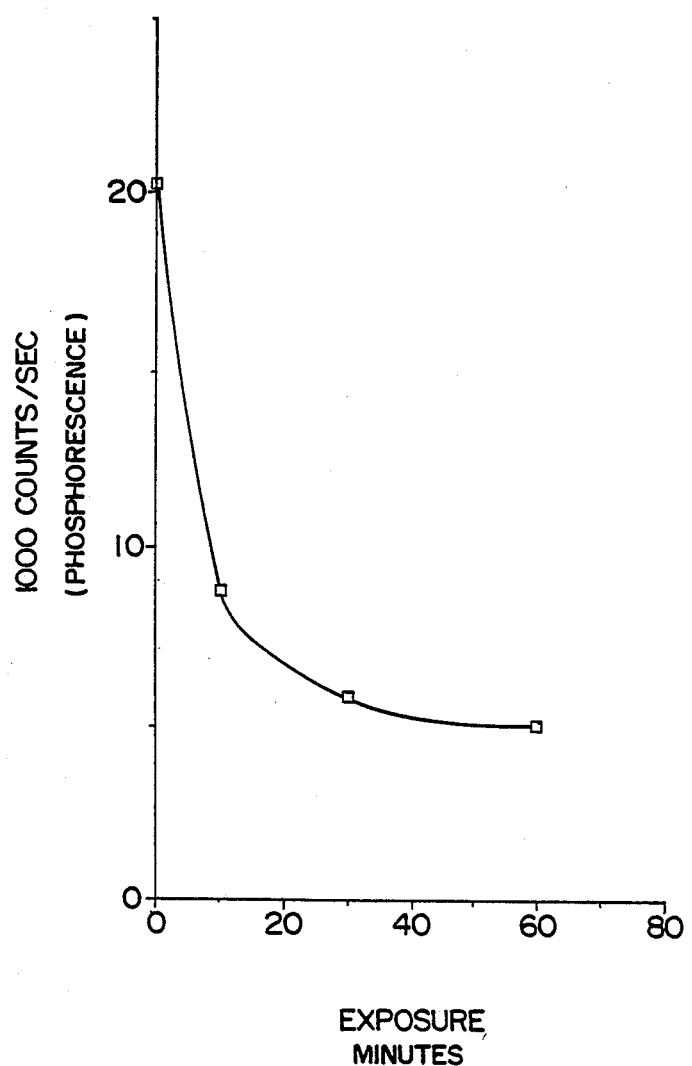
FIG. 3 is a graph showing the decrease in relative phosphorscence of the sensor as it is exposed to "Real Pine" household cleaner.

The subject of this invention is based upon the method shown in FIG. 1. In the method, a sensor 12 is attached to the inside surface of polymeric container 11. The sensor undergoes a change in optical density (i.e., opacity) upon exposure to a wide variety of contaminants. Usually the mechanism of this change in opacity is due to the contaminant dissolving in the sensor. This change in optical density can be detected by illuminating the sensor with ultraviolet radiation from a light source 13. A light detector 14 is used to measure the effect of the sensor on the ultraviolet illumination.

Various possible configurations for the light source and light detector are possible. For instance, in FIG. 1, the light detector is beneath the container, 180°. from the light source which is situated above the container opening. Another possibility, shown in FIG. 1A, is that the light detector is beside the light source above the container opening.

There are a number of different ways that this method could be utilized by the food and beverage industry. For instance, in the plastic beverage container industry, a sensor could be attached to the inside of a bottle (probably on the bottom surface) prior to the bottle being filled with a beverage. Attachment of the sensor could be made during the original manufacture of the bottle or could occur later. The sensor could be attached by gluing, welding, spray painting, and so forth.

The bottle is then filled with beverage and sold. After its use, the bottle is returned to a bottler for refilling. As part of the refilling process (or potentially in a separate operation prior to its refilling) the bottle is checked to see if the sensor has been contaminated. Since potentially millions of bottles must be checked for contamination, the method must be essentially instantaneous. Therefore, the method will probably be utilized on a moving container conveyor belt. As each container moves into position, it is exposed to ultraviolet light. A light detector then observes the effect of the sensor on the ultraviolet light and, in effect, determines the sensor's optical density.

By comparing the sensor's optical density (i.e., the reading from the light detector) with the optical density of an uncontaminated standard sensor, the bottle is either accepted or rejected as contaminated.

Typically the sensor has two components. One which changes opacity when exposed to the contaminants of interest and the second which goes through some detectable change when illuminated with UV light. The uncontaminated sensor must be transparent to the UV wavelengths for a pathlength sufficient for the light to reach the responsive component of the sensor. The rationale behind this sensor design lies in the fact that if the sensor becomes opaque to certain UV light when exposed to contaminants, the responsive component of the sensor will not "see" the UV light and thus does not respond as it would have had the sensor not been contaminated. The detector 14 will sense this difference in response and in effect tell whether the sensor may have been subjected to contamination. Since the plastic container can also absorb contaminants, it can be assumed that a contaminated sensor is representative of a contaminated plastic container. It is also possible that the UV responsive component is not in the sensor but in the plastic container itself.

The wavelength of ultraviolet light used to illuminate the sensor is most appropriately in the range of 200–300nm (nanometers). Surprisingly, most potential contaminants that plastic bottles may be exposed to have UV absorbing hydrocarbon components that have high extinction coefficients in the 200–300nm range. UV absorbing but non-hydrocarbon species more polar in nature are generally of less concern because they partition more favorably into an aqueous phase then into the plastic container.

The contamination absorbing component of the coupon should have several properties to give best contamination detection; it should absorb hydrocarbons at least as well as the composition of the container, but it should not extract large amounts of flavor components from the product intended to be held in the container.

Another potentially desirable quality of the contamination absorbing component is that if the coupon is subjected to contamination, it either dissolves or becomes detached from the container. See Example 2. When the UV light source illuminates the area where the coupon was attached, there is now no sensor and obviously no response from the sensor. The light detector senses this lack of response and it can be presumed that the container has been contaminated.

One factor that should be addressed when choosing the contamination absorbing component of the sensor is whether it will lose its opacity when exposure to the contaminants ceases. This could result in a reversion back to transparency faster than decontamination of the container. See Example 6.

Potential contamination absorbing components would include nontoxic, non-UV absorbing polymers such as polyisobutylene, methacrylate polymers and ethylene copolymers.

The preferred contamination absorbing component in the sensor is silicone rubber (crosslinked polydimethyl siloxane). Silicone rubber has most of the desirable properties described above. It has excellent transparency in the UV, it rapidly absorbs hydrocarbons (approximately $10^4$ times faster than PET), and its adhesion to the container material tested, polyethylene terephthalate, is destroyed by concentrated contaminants. See Example 2. Also, the sensor has surprising absorption selectivity for contaminants over hydrocarbon extractable components of beverages that may be packaged in reusable containers. In short, these beverages do not cause the silicone rubber sensors to become opaque even after prolonged exposure. See Example 5.

A variety of detection mechanisms can be employed in the ultraviolet light responsive component of the sensor. These include reflectance by a metallic layer or by light scattering from a dispersed phase having a different refractive index than the absorbing component. (In this case, the reflected light would be the same wavelength as the light source.) For this detection method, less reflectance would result after sensor contamination because the contamination absorbing component becomes opaque. This method is discussed in Example 4. In principle, discrimination of stray light from light reflected from the sensor can be achieved. However, the requirements of the detection instrument for this method are more constrained than for some other detection methods.

In Example 4, transmission of UV was attenuated by a contaminant absorbed into a silicone rubber sensor. The detector is on the other side of the sensor, 180° from the light source. If the detector were coaxial (360°) with respect to the light source instead of 180°, light scattered from the filler in the silicone rubber would be detectable and would be modulated by the presence of UV absorbing material. The disadvantage of monitoring the change of absorbance with the detector located 180° with respect to the light source is that the beam of UV must pass through the wall of the container. Very few polymers are sufficiently transparent to short wavelength UV light, and of those that are, most are not useful as food container materials.

Another potential means of detection of modulation of the responsive component is detection in a fluorescence mode. In this mode the re-emitted light is measured at the same time the sensor is exposed to the ultraviolet light source. This method is demonstrated in Example 3. In this case, the re-emitted light can be a sufficiently long wavelength to penetrate the container, and the detector can be located 180° with respect to the light source (i.e., on the other side of the polymeric container). Also, most stray light can be removed by placing an appropriate filter between the detector and the coupon. In this embodiment, the container itself can be the responsive component, if it fluoresces when excited by UV light.

However, the choice of an appropriate fluorophor is complicated by the fact that many UV absorbing organic materials are fluorescent, including both potential contaminants and natural components of the material intended to be held in the container. Analysis of the intensity of the fluorescence as a function of wavelength could reduce this interference, and may eliminate it in some cases.

The preferred detection method employs phosphorescence detection, where the sensor is illuminated with UV light to excite the responsive component, which is a phosphor. After the ultraviolet light is extinguished, there is a time delay before detection of the re-emitted light.

The advantage of using a phosphorescent responsive component compared to a fluorescent or reflective one is that it is exceedingly unlikely that phosphorescent contaminants could absorb into the sensor and thereby cause false negative tests. Hydrocarbons that phosphoresce do so only at cryogenic temperatures. The fluorescence of organic compounds generally has a half-life in the range of nanoseconds to hundreds of nanoseconds, so a delay of only one microsecond after illumination of the coupon and before detection of the re-emitted light will be sufficient to allow decay of any prompt fluorescence from contaminants or beverage residues.

Phosphors potentially suitable as the responsive component are preferably selected from inorganic pigments such as $ZnS:Mn$, $ZnSi:Cu$, $Zn_2SiO_4$, $ZnS:Mn:Cu$, $ZnS:Cu$, $Ca_5(F,Cl)(PO_4)_3:Sb:Mn$, $Ca_5F(PO_4)_3:Sb:Mn$, $(Ba,Ti)_2P_2O_7:Ti$, $Sr_2P_2O_7:Sn$, $Ca_5F(PO_4)_3:Sb$, $Sr_5F(PO_4)_3:Sb:Mn$, $BaMg_2Al_{16}O_{27}:Eu$, $Sr_5Cl(PO_4)_3:Eu$, $Sr_5(F,Cl)(PO_4)_3:Sb:Mn$, $(Ca,Mg,Zn)_3(PO_4)_2:Sn$, $(Sr,Mg)_3(PO_4)_2:Sn$, $CaSiO_3:Pb:Mn$, $Zn_2SiO_4Mn$, $(Ce,Tb)MgAl_{11}O_{13}:Ce:Tb$, $MgWO_4$, $Li_2Al_2O_4:Fe$, $Y_2O_3:Eu$, $Mg_4(F)GeO_6:Mn$, $Mg_4(F)(Ge,Sn)O_6:Mn$, $CaWO_4:Pb$. These pigments have light emission decay constants in the range of microseconds to about one second. Factors such as cost and potential toxicity would need to be explored.

An additional advantage of these phosphors is that they often have extremely large difference in excitation and emission wavelengths. They can be excited by 200–300nm light, but often re-emit at wavelengths greater than 400nm. If detection is not through the opening of the container, this is highly desirable for UV opaque and tinted containers.

PREFERRED EMBODIMENT

In a preferred embodiment, the sensor has two layers. See FIG. 2. The top layer 12c is the contamination absorbing component of the sensor and consists essentially of clear silicon rubber. The advantages of silicone rubber were previously discussed. The bottom layer 12b consists essentially of clear silicon rubber and zinc sulfide phosphor. The zinc sulfide phosphor is the UV responsive component of the sensor.

From FIG. 1A the UV light source 13a emits light in the 200–300nm range and the detector 14a detects light in the 450–550nm range at least one microsecond after exposure of the sensor to UV light from the light source.

The light source would give a short (microsecond) burst of 200–300nm light. If the sensor is uncontaminated, the 200–300nm light passes into the sensor, excites the zinc sulfide phosphor, and it re-emits light between 450–550nm with a decay time constant of between one millisecond and one second. Another possibility, in PET containers, is that the ultraviolet light passes through both layers of the sensor and excites the inherent fluorescence of the PET. This results in effective emission of light from the PET at about 400nm that is also effective for excitation of the zinc sulfide phosphor.

If the light detection is delayed more than a microsecond, any prompt fluorescence of the container and residual beverages will be gone and undetectable. The yield of re-emitted light will be proportional to the amount of light that penetrated the silicone rubber. If the silicone rubber has extracted material from a contaminant that strongly absorbs light at 200–300nm, the yield of re-emitted light will be attenuated.

In our most preferred embodiment the sensor contains two phosphors rather than one. This is important because of possible interference to the geometric light path of the excitation and/or re-emitted light by imperfections in the bottle, and/or sensor. For example, if the light detector is at the side of the bottle then any scratches, scuffs, dents, flutes and so forth in the bottle or imperfections in the sensor or in the placement of the sensor may cause attenuation of the re-emitted light from the phosphor and give erroneous readings.

This problem can be minimized by the addition of a second "pilot" phosphor. The pilot phosphor is excited by light of a wavelength greater than 300nm and thus is unaffected if the sensor absorbs the contaminants of interest (contaminants which absorb UV light in the 200–300 nm range). The pilot phosphor can be discriminated from the response phosphor by differences in the emission ranges or in the time response of the emission. If the two light detectors are receiving light from the same area it can be assumed that these interferences will affect the re-emitted light from the response and pilot phosphors to the same degree. Thus attenuation of the response phosphor re-emitted light from any type of interference can be compensated by comparing it to the pilot phosphor re-emitted light.

In our most preferred embodiment, use of the second phosphor with distinct emission range has the following modifications to the preferred embodiment described above: (1) the light source has two ranges (200–300 nm for the response and greater than 300nm for the pilot); (2) the detector has two ranges (450–550 nm for the response and greater than 550 nm for the pilot). In the sensor the response phosphor is zinc silicate doped with manganese. This phosphor is commercially available from Sylvania as phosphor type 2283. The pilot phosphor is zinc sulfide doped with manganese and copper. It is available from Sylvania as phosphor type 523. For those skilled in the art it will be obvious that other phosphors and wavelength ranges could be substited.

Figure 8:
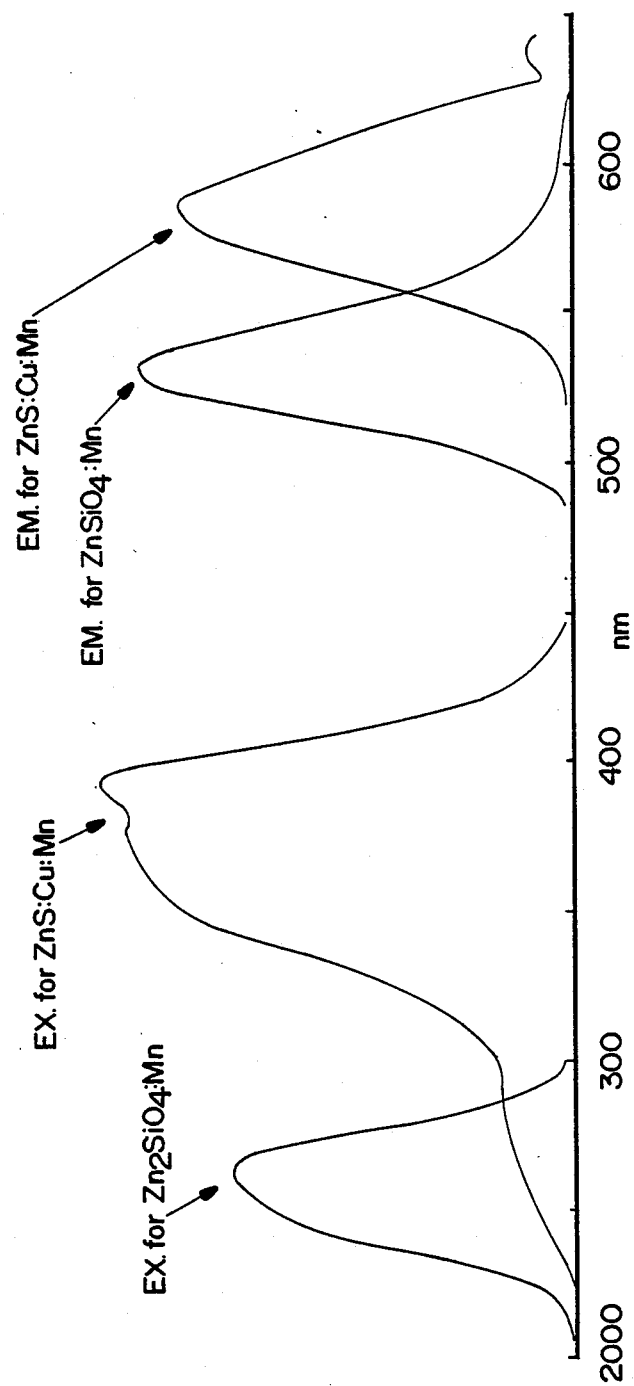
FIG. 8 is a graph of the excitation and emission spectra for two phosphors.

In this embodiment the light source emits a microsecond burst of two ranges of light (one in the 200-300 nm range and the other in the 350-450 nm range). The response phosphor (zinc silicate doped with manganese) re-emits light in the 500-550 nm range. The pilot phosphor (zinc sulfide doped with copper and manganese) re-emits light in the 540-620 nm range, as is shown in FIG. 8. In this embodiment there are two light detectors which are located on the outside of the bottle such that the re-emitted light from the phosphors must travel through the bottle structure before it reaches the detectors. The response phosphor re-emitted light detector detects light in the 450-550 nm range at least one microsecond after the exposure of the sensor to light in the 200-300 nm range. The pilot phosphor re-emitted light detector detects light in the 580-620 nm range at least one microsecond after the burst of light in the 400-450 nm range.

The light source emission ranges may be accomplished by filtering the light not in the desired ranges from a panchromatic source such as a xenon flash lamp or from a "line" source such as a mercury vapor lamp. Another possibility is using two different light sources whose beams are combined.

Example 7 below shows that the pilot phosphor (zinc sulfide doped with copper and manganese) does not interfere with detection of the contaminants by the response phosphor (zinc sulfide doped with manganese). Furthermore, Example 7 shows that the pilot phosphor is not affected by the contaminating substances.

EXAMPLES

The following examples clearly illustrate the basic concepts of the invention. However, in none of the examples was a sensor actually attached to the inside of a plastic bottle or used in an actual beverage filling process.

EXAMPLE 1

Phosphorescence Detection

This example illustrates how a sensor's phosphorescence decreases after exposure to a wide variety of contaminants.

A sample of 10 parts of silicone RTV (moisture curable polydimethyl siloxane, type 732, Dow Corning) was dissolved in 15 ml of 1,1,1-trichloroethane (TCE). After dissolution, one gram of ZnS:Cu phosphorescent pigment (series 1000 pigment from Conrad-Hanovia) was mixed in, and the suspension was coated onto 5 mil (one thousandth of an inch) thick polyethylene terephthalate film. The coating was applied using a doctor knife with shims such that the final film thickness after drying and curing was approximately 2.5 mil.

After curing, the above film was then recoated with a layer of 5 mil (after drying) of clear silicone rubber using a coating mixture of 15 parts of TCE and 10 parts of uncured RTV. After this layer cured, the film was cut into 0.9×4 cm strips for testing. The two layer composition will be referred to as a sensor.

The testing was done by immersing the strips in test fluids, and determining the effect after defined time periods. The instrument used was an SLM 8000 fluorimeter with a rotating can cuvette holder. The film samples were held at a 45° angle with respect to the excitation and emission positions. The phosphorescence measurements were recorded one minute after placement into the instrument to minimize the effect of room lighting in the laboratory. The excitation wavelength was 250nm and emission was 500nm.

The typical response of a sensor to contamination is shown in FIG. 3. The phosphorescent response of the contaminated sensor as a function of time s compared to the phosphorescent response of a reference sensor that has not been exposed to the contaminant. In this case, "Real Pine" household cleaner was exposed to the sensor at user strength. As can be seen from the graph, relative phosphorescence decreases quickly and dramatically after exposure to the household cleaner.

Similar results were obtained with most other contaminants of interest as can be seen from Table I. This table represents a summation of the data from experiments similar to the household cleaner experiment shown in FIG. 3. Results were tabulated as positive (+) if the coupon lost more than 50% of its phosphorescence response within three days of exposure.

The two contaminants not detected were methanol and potassium cyanide, neither of which absorb 250nm light.

TABLE 1

| Material | Response |
| --- | --- |
| Volk ® (Preemergent Spray) (Chevron Chemical Co.) | + |
| 2,4,5-T (Clover) (Black Leaf Products Co.) | + |
| Nicotine (Black Leaf 40)* (Black Leaf Products Co.) | + |
| Lindane ® (Chevron Chemical Co.) | + |
| Sevin ® (Chevron Chemical Co.) | + |
| Diazinon ® (Chevron Chemical Co.) | + |
| Malathion ® (K-Mart Corp.) | + |
| Chlorodane ® (Gabriel Chemicals Ltd.) | + |
| Endosulfan ® (Thiodan) (Dragon Chemical Corp.) | + |
| Cygon 2E ® (Dimethoate) | + |
| Real Pine ® (Pine Scented Cleaner) (White Cap, Inc.) | + |
| Methanol | — |
| Potassium Cyanide | — |

*The phosphorescence loss was close to 50%.

EXAMPLE 2

Detection of Contaminants by Loss of the Coupon

The sensors described above in Example 1 were exposed to concentrated hydrocarbon contaminants, and the time required for the coupons to delaminate from the PET film substrate was recorded. The results are recorded in Table 2.

TABLE 2

| Contaminant | Time Required for Delamination |
| --- | --- |
| Benzene | 50 min. |
| Gasoline | 10 min. |
| Paint Thinner | 50 min. |
| Carbon Tetrachloride | 10 min. |
| Pentachlorophenol (Woodlife ®) | 50 min. |
| Trichloroethylene | 2 min. |

EXAMPLE 3

Contamination Detection using Fluorescence Detection

This example shows how fluorescence of the sensor decreases after exposure to contaminants of interest.

A slurry of ZnS:Cu (0.4 g) in a solution of silicone rubber (0.3 g) in TCE (4 ml) was coated onto 4 mil polyethylene terephthalate film as in Example 1. After curing, it was overcoated with a clear silicone rubber, as before. The film was cut into strips and exposed overnight to pesticides diluted into water at user strength, as described on the pesticide bottle. The fluorescence was measured as in Example 1 (except that there was no rotating can/cuvette), and the result was compared to the signal from a reference beam. The results are listed below in Table 3.

TABLE 3

| Contaminant | % Response of Control |
|---|---|
| Control | 100 |
| Volk ® | 80 |
| Sevin ® | 63 |
| Diazinon ® | 23 |
| Malathion ® | 67 |
| Chlorodane ® | 38 |

EXAMPLE 4

Detection of Contaminants Using the Sensor's Optical Absorbance

This example illustrates how a sensor with no fluorophor or phosphor might be used to detect potential contamination using the sensor's optical absorbance.

Figure 4:
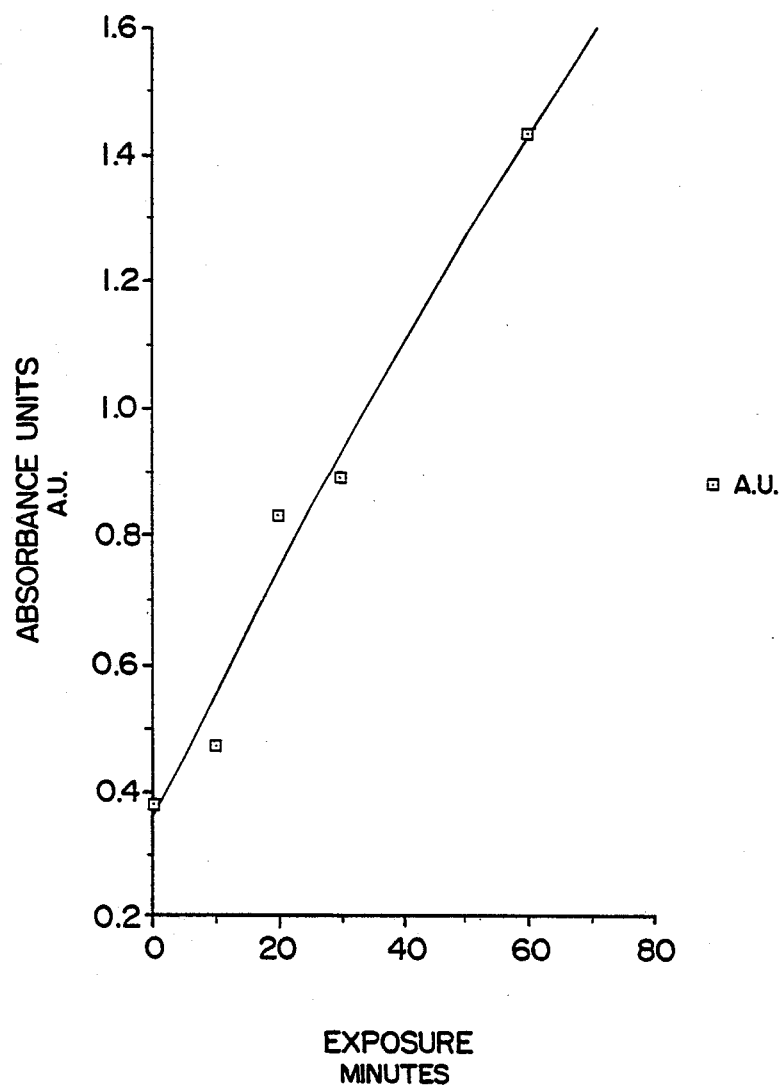
FIG. 4 is a graph showing the increase in optical absorbance of a sensor as it is exposed to the pesticide Thiodan ®.

A sensor was applied using a mixture of 15 parts (by volume) of TCE and 10 parts (by weight in grams) of RTV. The clear silicone sensor was mounted on Teflon ® FEP film. The sensor had no fluorophor or phosphor. Thiodan ®, a common pesticide, was diluted into water at user strength defined by the manufacturer. The optical absorbance (at 280nm) of sensors exposed to this mixture was monitored as a function of time. The loss of transparency is due to dissolved contaminant building up in the sensor. After 13hours, the optical density was too high to measure. The result is shown in FIG. 4.

In this embodiment, contaminants can be detected by the change of optical absorbance directly by placing a light detector on the other side of the sensor, 180° from the light source. This mode will only work if the container is transparent to ultraviolet light. However, an equivalent result could be achieved by including a reflective component in the sensor so that the light attenuation could be detected without the requirement that it pass through the container (i.e., with the light detector 360° from the light source).

EXAMPLE 5

The effect of Beverages on Coupons

Figure 5:
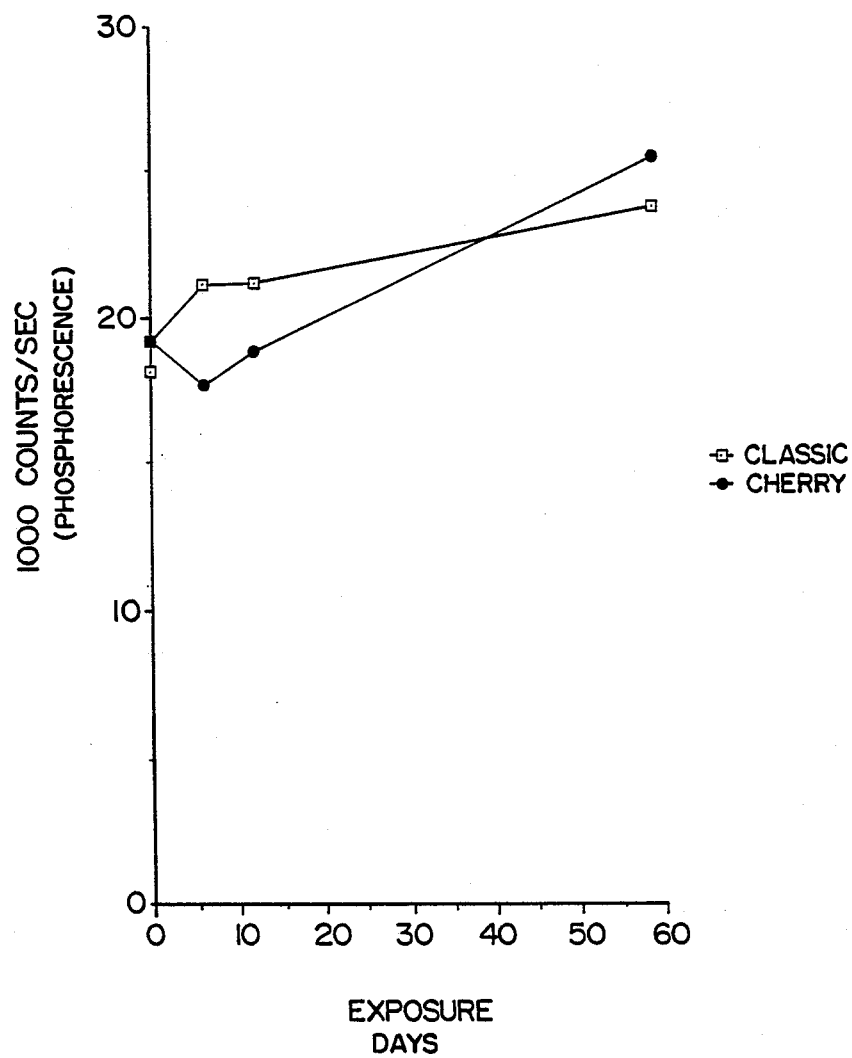
FIG. 5 is a graph showing the relative phosphorescence of sensors after long-term exposure to "Cherry Coke" and "Coke Classic."

It is important that the sensor not be affected by the intended contents of the reusable container. This example shows that, in a phosphorescence mode, the sensors are not modified by long-term exposure to beverages. Sensors (made as in Example 1) were exposed to two commonly consumed beverages, "Coke Classic" and "Cherry Coke." The sample coupons were immersed in the test beverages at 50° C., and periodically tested for phosphorescence response (thousand counts per second). No significant change was seen after 60 days as can be seen from FIG. 5. Each data point for the beverage exposure study is the average value measured on ten coupons.

Figure 6:
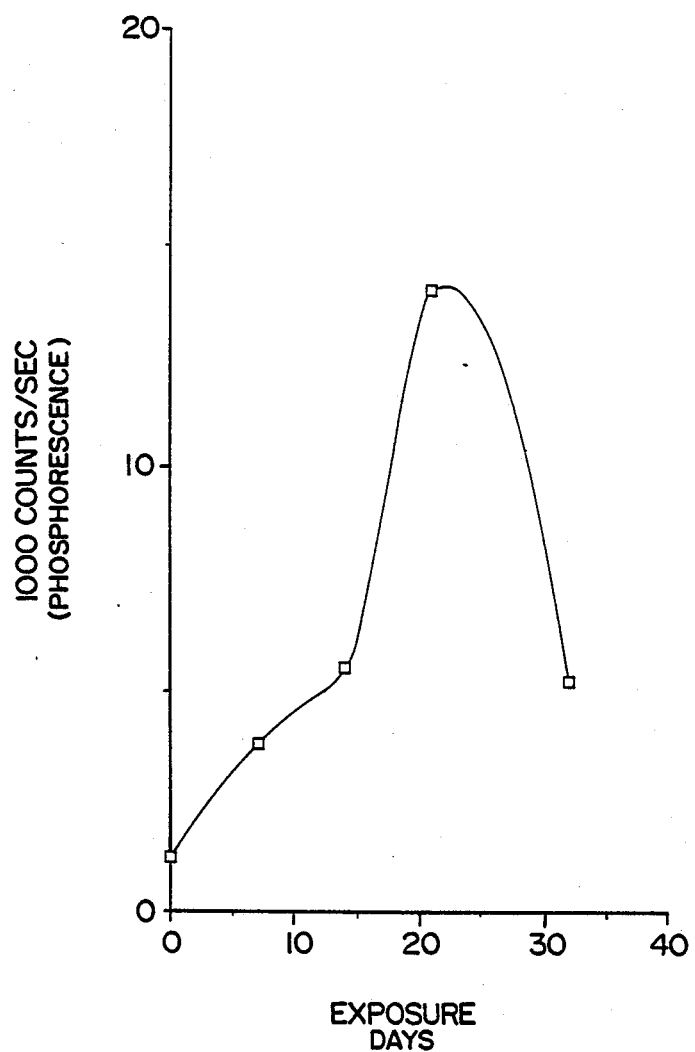
FIG. 6 is a graph showing the relative fluorescence of a sensor after long-term exposure to "Cherry Coke."

Sensors were also prepared by coating polyethylene terephthalate with a layer of 38% weight by volume (W/V) silicone and 10% (W/V) of ZnS:Cu in TCE. After curing, a clear layer was added using 38% (W/V) of silicone rubber. The sensors were then exposed to "Cherry Coke" as above and their fluorescence measured. The results are shown in FIG. 6. As can be seen, the response of the instrument in a fluorescent mode changed with exposure time. This result was surprising in light of the results obtained using phosphorescence measurements.

Figure 7:
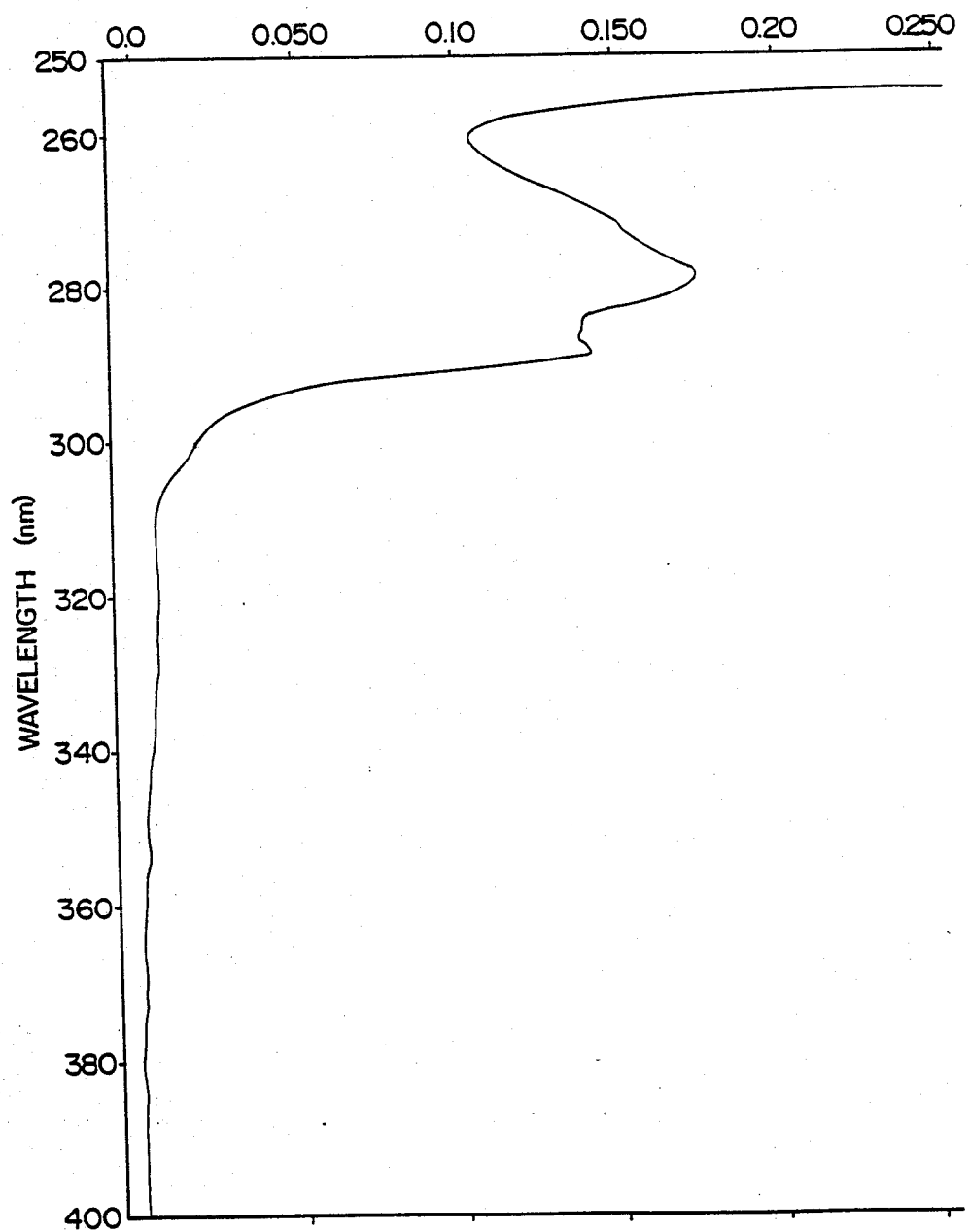
FIG. 7 is a graph showing the absorbance of components which were extracted from "Cherry Coke" using a non-polar solvent.

It is also surprising that the sensor was not rendered opaque b extraction of hydrocarbon type components from the beverages. When "Cherry Coke" was extracted with a non-polar solvent (hexadecane), there is obviously UV absorbing extractable material. (See FIG. 7).

EXAMPLE 6

Sensor Reversion Back to Transparency

A sensor (made as in Example 1) was exposed to Thiodan (as in Example 4) for one week. After the one week exposure, the sensor had become very cloudy. The optical absorbance of the sensor was then determined at regular intervals after its removal from the Thiodan. The results are recorded in Table 4 below.

TABLE 4

| Hours After Exposure | Optical Absorbance |
|---|---|
| 0 | Greater then 3.0 |
| 15.5 | 2.8 |
| 24.5 | Greater than 3.0 |
| 40 | 2.5 |

EXAMPLE 7

Two Phosphor Sensor Performance

The sensors were made in a manner similar to those described in axample 1. Two grams of RTV were dissolve in 3 ml of TCE. To this was added 1 g of Sylvania 523 and 0.75 g of Sylvania 2283 phosphors. The coating process and testing of the sensors were the same as in example 1, except that the immersion time was 7 days. The response to various contaminants is listed in table 5 below as percent of retained phosphorescence after the sensors had been washed in 1 N sodium hydroxide at 70 deg. C. for 10 minutes.

TABLE 5

| MATERIAL TESTED | % RETAINED PHOSPORESCENCE |
|---|---|
| Ethyl parathion (Bayer) | 0 |
| Metasystox ® (Bayer) | 3.1 |
| Chloridazon ® (BASF) | 0.2 |
| Prochloraz ® | 0.5 |
| Triadimeton ® (Bayer) | 1.2 |
| Orthochlor ® (Chevron) | 0.4 |
| Maneb (Agway) | 65 |
| Motor oil (Briggs and Straton) | 3.0 |
| Volk ® (preemergent spray) | 10 |
| 2,4,5-T | 3.7 |
| Nicotine | 2.0 |
| Lindane | 0.1 |
| Sevin ® | 4.2 |
| Diazinon | 0.08 |
| Malathion | 0.4 |
| Chlorodane | 0.2 |
| Thiodan ® | 0.9 |
| Cygon 2E ® | 0.4 |
| Real Pine ® Cleaner | 0.2 |

When the test samples were illuminated with long wavelength UV-light (365 nm) the orange phosphorescence (re-emitted light from the pilot phosphor) did not appear visually to be attenuated in any of the test sensors, while the green phosphorescence (re-emitted light from the response phosphor) from short wavelength UV light (254 nm) was observed to be highly attenuated by simple visual inspection.

We claim:

1. A method for determining whether certain contaminants are on or have migrated into the body of a plastic reusable food or beverage container comprising:
   (a) attaching a sensor to the inside of the container which sensor undergoes a detectable change in its optical density when exposed to the contaminants;
   (b) determining the optical density of the sensor by exposing the sensor to ultraviolet illumination and measuring the effect of the sensor on the ultraviolet illumination;
   (c) comparing the optical density of the sensor with the optical density of an uncontaminated standard sensor.

2. The method of claim 1 where the sensor comprises two components; one which responds when exposed to ultraviolet light and the second which changes opacity when exposed to said contaminants.

3. The method of claim 2 where the responsive component is phosphorescent or fluorescent.

4. The method of claim 3 wherein the component which changes opacity when exposed to contaminants is a nontoxic, nonultraviolet light absorbing polymer.

5. The method of claim 4 wherein the phosphorescent component of the sensor comprises an inorganic pigment.

6. The method of claim 5 wherein the sensor is illuminated with ultraviolet light between 200 and 300 nanometers.

7. The method of claim 6 wherein the optical density of the sensor is determined using a light detector operating in a range most appropriate for measuring the fluorescence or phosphorescence of the sensor.

8. The method of claim 7 wherein the light detector measures phosphorescence of the sensor at least one microsecond after exposure to the ultraviolet light.

9. The method of claim 8 where the sensor comprises clear silicon rubber and zinc sulfide phosphor.

10. The method of claim 9 where the sensor comprises two layers; a top layer, and a bottom layer, which is attached to the container; the top layer consisting essentially of a clear silicon rubber, and the bottom layer consisting essentially of zinc sulfide phosphor and clear silicon rubber.

11. The method of claim 10 wherein the light detector operates in a range between 450 and 550 nanometers.

12. The method of claim 3 wherein the responsive component comprises a response phosphor and a pilot phosphor.

13. The method of claim 12 wherein the pilot phosphor is used as reference in order to correct for optical interferences.

14. The method in claim 2 wherein the responsive component is reflective.

15. The method of claim 14 wherein the reflective component is a metallic surface or a dispersed phase having a different refractive index than the second component.

16. The method of claim 1 wherein the optical density of the sensor is determined by measuring the response of the plastic container to the ultraviolet illumination passing through the sensor.

17. A method for determining whether contaminants have migrated into the body of a plastic reusable food or beverage container comprising:
   (a) attaching a sensor to the inside of the container, which sensor being detached or dissolved when exposed to the contaminants;
   (b) determining the presence or absence of the sensor by exposing the area of the container where the sensor was attached to ultraviolet light and measuring the effect of said area on the ultraviolet illumination.

18. A sensor used for determining whether contaminants are on or have migrated into the body of a plastic reusable food or beverage container comprising two components, one which responds when exposed to ultraviolet illumination and the second which changes opacity when exposed to the contaminants.

19. The sensor of claim 18 comprising clear silicone rubber and zinc sulfide phosphor.

20. The sensor of claim 19 comprising two layers; a top layer, and a bottom layer, which is attached to the container; the top layer consisting essentially of clear silicon rubber, and the bottom layer consisting essentially of zinc sulfide phosphor and clear silicon rubber.

21. A plastic reusable food or beverage container with a sensor attached to the inside of the container, which sensor is used for determining whether contaminants are on or have migrated into the body of the container, such sensor comprising two components, one which responds when exposed to ultraviolet illumination and the second which changes opacity when exposed to the selected contaminants.

22. The container of claim 21 wherein the sensor comprises clear silicon rubber and zinc sulfide phosphor.

23. The container of claim 22 wherein the sensor comprises two layers; a top layer and a bottom layer, which is attached to the container; the top layer consisting essentially of clear silicon rubber, and the bottom layer consisting essentially of zinc sulfide and clear silicon rubber.

* * * * *